United States Patent
Amson et al.

(10) Patent No.: US 6,956,110 B1
(45) Date of Patent: Oct. 18, 2005

(54) GENES INVOLVED IN THE MOLECULAR PATHS OF TUMOR SUPPRESSION AND/OR RESISTANCE TO VIRUSES

(75) Inventors: Robert Amson, Paris (FR); Adam Telerman, Paris (FR)

(73) Assignee: Molecular Engine Laboratories, Paris (FR)

( * ) Notice: Subject to any disclaimer, the term of this patent is extended or adjusted under 35 U.S.C. 154(b) by 0 days.

(21) Appl. No.: 09/762,249

(22) PCT Filed: Jun. 18, 1999

(86) PCT No.: PCT/FR99/01479

§ 371 (c)(1),
(2), (4) Date: Feb. 5, 2001

(87) PCT Pub. No.: WO00/08147

PCT Pub. Date: Feb. 17, 2000

(30) Foreign Application Priority Data

Aug. 5, 1998 (FR) .............................. 98 10077

(51) Int. Cl.⁷ .................. C07H 21/02; C12N 15/63; C12N 5/00
(52) U.S. Cl. .................. 536/23.1; 435/320.1; 435/325
(58) Field of Search .............................. 435/320.1, 325; 536/23.1, 23.5

(56) References Cited

FOREIGN PATENT DOCUMENTS

WO    95/20654 A1    8/1995
WO    97/22695 A2    6/1997

OTHER PUBLICATIONS

Roperch et al. SIAH-1 promotes apoptosis and tumor suppression through a network involving the regulation of protein folding, unfolding, and trafficking: identification of common effectors with p53 and p21Waf1. Proc. Natl. Acad. Sci. USA 96:8070–8073, 1999.*

Advani et al. Seven novel mammalian SNARE proteins localize to distinct membrane compartments. J of Biological Chemistry 273:10317–10324, 1998.*

Robert B. Amson, et al.; "Isolation of 10 Differentially Expressed cDNAs in P53–Induced Apoptois: Activation of the Vertebrate Homologue of the *Drosophila* Seven in Absentia Gene"; Proc. Nat'l Acad. Sci. USA, vol. 93, pp. 3953–3957; Apr. 1996.

Robert Strausberg, Ph.D.; "EST. H. Sapiens cDNA Clone Image: 1556458"; Database GENBANK 'Online!; Accession No. AA935282; Jun. 23, 1998.

Robert Strausberg, Ph.D.; "EST. H. Sapiens cDNA Clone Image: 1650253, Similar to T–complex Protein 1 (TCP–1) Epsilon Subunit", Database GENBANK 'Online!; Accession No.A1022498; Jun. 19, 1998.

Mona Nemani et al.; "Activation of the Human Homologue of the *Drosophia sina* Gene in Apoptosis and Tumor Suppression"; Proc. Nat'l Acad. Sci. USA, vol. 93, pp. 9039–9042, Aug. 1996.

Jean–Peierre Roperch, et al.; "Inhibition of Presenilin 1 Expression is Promoted by p. 53 and p. 21 WA–$^{WAF-1}$ and Results in Apoptosis and Tumor Suppression", Nature Medicine, vol. 4, No. 7, pp. 835–838, Jul. 1998.

David Israeli, et al.; "A Novel p. 53–Inducible Gene, PAG608, Encodes a Nuclear Zinc Finger Protein Whole Overexpression Promotes Apoptosis"; The EMBO Journal, vol. 16, No. 14, pp. 4384–4392, 1997.

Gustavo Linares–Cruz, et al.; "p. 21 $^{WAF-1}$ Reorganizes the Nucleus in Tumor Suppression"; Proc. Nat'l Acad. Sci. USA; vol. 95, pp. 1131–1135, Feb. 1998.

* cited by examiner

*Primary Examiner*—Ram R. Shukla
(74) *Attorney, Agent, or Firm*—Foley & Lardner LLP

(57) ABSTRACT

The invention concerns genes involved in the molecular paths for tumor suppression and/or resistance to viruses, and whereof the cell expression is in particular induced or inhibited during apoptosis and/or tumor suppression.

6 Claims, 2 Drawing Sheets

TTTTTTTTTTTTTTTTTTTTTTTTTTAACAAAGCAGAGGGGTTTATTATAGGAAC
ATTCTCAAACTGCAACGGAAAAGATGTCCGTACAGGTGGATGGGGATGGAG
ATCCACCTCGGAGTACACAGACTTCAGGGGGCCTCCTGCCTGGCACGTTCTT
TCTCTCCCGTATCACCTAAGACCCTGAGACCTCCACCCTCTGCAGGAGAGAC
CCACAAAGAAGCCTCCTCCCTGTGGCCTGGCTCCCATCAGGGACAGTCCTGT
TTTTAGAGCAAGAACAGTCTGTACTTCAGACAGGATCCCAACCCCCACCCAA
ATTCAATGTCGACCGTCTGAGCAGCAGCTTCATTGGCTGCAAACGCCTCTC
TCAGGTGAGTCAAAGGAGACACGACGGGGAACCAGGGGCCCTAGGTGAGG
ATGTCATGGGCCTGGTGCTCCACCAGCATCTCCATGCTCTTCACATCCGTGC
ACCAGAACTCCAGGCGGTCCTTCATTCCCTTGATCTGTTGCAAATCCAACAC
TCGGGGCTGCACCCAGGTCATGTGGACTCGTTTGTCCACCTCGTCTATACTG
CCTTTCACCAGCCCCACCGAAAGGGCCTTCATCACCAGAAGCTCCACCTCAT
TCACTGTGATTTTAGCACTTTTGGCAATTTCTTCAAAAGTGACTTGTCTGTGA
TTGGCAGGTCGTGTGAAAGTCATCTCCATGAGGCACAACAACTGAATTTTCC
TCAGAAGCTGGGCTTCATTAGCTGCTAAATCAGGCTGCTGGCCCGAGGCAGT
CTTCAGAGTCTGGAACCGCTCTACGTTGCCACTGTTGAAGGCATAGAGGGTG
TCAATCAGCCACTGCCGGTCAGTATTCCTCAGGGACTCCAGCACAGGGTGCA
TGAGGAGTTCTCCAAAGTTAAAAACTCCCTCGCCGAGAAGTCCTGCTAGCCC
CAGCGTGAAGGCTCTCTCCTGCTGCTCAGACACTGGTAGATCCTTGATGTCA
ACACAGCCCAAAAACCGCAGAGCATCTTTGTAGTAGGACGCGTGGTTTCCGA
TTGTTTGATAGTATTTACTGGAGAGATCATAGAAACGACTGTGAACCGATGT
CACACCAGGAAGGTTGTTGAGCATTTCTTCAACATCTTCAATTGTTTCCTTTG
TAACCTGTAGGTCCCCGATGTTTAATTTTAGAGCTCCAATTGCTGTTTTACAC
AGGATCACTGCCTCATCACTACTTTTCACCTTCTCACGAGTCTTTTCCAGAAA
AGTAAGAGCCACATTAGGATCAGTCATCTGTCTAACTACGTGAAGAATGATT
TCCACGAGGGACAGAGGATTCACCCTGTGTTCAAATTCACTGATAAAGTTTT
CATAAAGCTTAATGAGACCATCTCCTTGGGCAAAGCACGGATCCTGCACAAA
ATCAAGCACCTGAAGTGTCAGCTGATGCCACAACTTCTTCGTGTAGAGCTCC
TCCAGACGGTGCCACACAGCGGGCTGCCCGGGCCCGAGCTCTGGCTCTGC
TGTAGGAAGCCCGGTACGTCCTTCATGACAGCAGG

FIGURE 1

```
ATCCAGCGCCAGCTGGAGATCATGGGCAAGGAAGTCTCGGGCGACCAGATC
GAGGACATGTTCGAGCAGGGTAAGTGGGACGTGTTTTCCGAGAACTTGCTG
GCCGACGTGAAGGGCGCGCGGGCCGCCCTCAACGAGATCGAGAGCCGCCAC
CGCGAACTGCTGCGCCTGGAGAGCCGCATCCGCGACGTACACGAGCTCTTC
TTGCAGATGGCGGTGCTGGTGGAGAAGCAGGCCGACACCCTGAACGTCATC
GAGCTCAACGTACAAAAGACGGTCGACTACACCGGCCAGGCCAAGGCGCAG
GTGCGGAAGGCCGTGCAGTACGAGGAGAAGAACCCCTGCCGGACCCTCTGC
TGCTTCTGCTGTCCCTGCCTCAAGTAGCAGGCCGGCCCGGGCCGCCACCGC
CCATCCCAGACCATGGAGCGCGCTGGGAAGGACGTCACCAAAGCCGGGAGC
TCTGCCCTGCAGGGAGTTGCCCCAACCCTTTCCGGAACTCAGTCTTTAGAAA
AGAAACGCCAGGTTCAAGAATTGCAAACCAGCCTGTGCTTGGAAAGATGGTT
AGTTGATACCGTGCGATGATTCTTCAGTAAAGATAGATTCCCACAAAGTTGTG
CAATGTCATTATATGACACCTTGCACTCTTACCGTCTTGACAGAAGCCAAGTAAGG
AACTGAAGTTGTATCTGACTGTAGGGTGAATGTCTGAGGCCTGCCTCCTAATAAA
GACTCAAGGAGGAAGTCAATTGGGCATCTGCTAATAGAATGAACTCATGATGGAA
ACTTCAGTTCATTTACTTTGTCCCTGAAAATTCCCTGGTTCTGTTCCATTTTGAGCG
AAATTGGCCTTGGGAAAAACCACGTTCTTCCTTTCCGATTCTTCATCCGGTCTACG
GCTATGCAATTCCTCCCCAAATATAGATCTTATTTCTGCTCATTTCCCCTACTTATT
AAAATCACACCAAACACTTACTATTTTCTTATCTCTTTCACTTTTTAAATATCTTTC
ACCAGGTTATATTTTGGTATTATTTTTCCAAACATTTTTAAGCACTGAATATCGAA
CAAGCACTCAAATTGAAGTATCAGTCATGTTTTGTGTATTTTTCGCTGATAAAAAT
TATTTAACATTTATATTTTTACTTGATTACATATGCACATGTATGTAAATGTAAAAT
ACTAATATTCACTAATATATGTACATAATGATCAATTGGTTTAACTTCTTTTATGTA
AGTATGGTATATAAATTTCAAGACGAAAAAAAAAAAAAAAAAAAAAAAAAAA
AAAAAA
```

FIGURE 2

SEQUENCE LISTING

<160> NUMBER OF SEQ ID NOS: 15

<210> SEQ ID NO 1
<211> LENGTH: 303
<212> TYPE: DNA
<213> ORGANISM: Homo sapiens
<220> FEATURE:
<223> OTHER INFORMATION: TSAP9

<400> SEQUENCE: 1

```
tcggtcatag tctggatggg attcatgata tgaagcaaca gcatgtcata gaaaccttga      60
ttggcaaaaa gcaacagata tctcttgcaa cacaaatggt tagaatgatt ttgaagattg     120
atgacattcg taagcctgga gaatctgaag aatgaagaca ttgagaaaac tatgtagtaa     180
gatccacttc tgtgattaag taaatggatg tctcgtgatg cgtctacagt tatttattgt     240
tacatccttt tccagacact gtagatgcta taataaaaat agctgtttgg ttaaaaaaaa     300
aaa                                                                    303
```

<210> SEQ ID NO 2
<211> LENGTH: 1356
<212> TYPE: DNA
<213> ORGANISM: Homo sapiens
<220> FEATURE:
<223> OTHER INFORMATION: TSAP10

<400> SEQUENCE: 2

```
tgagcagggc gacggcggcg gtggaacctg cggggctggg gcgccgccat gggcgcctgc      60
```

-continued

```
actgcactga ggacccggtg ccggaccggt gggcggcgac atgcagcagc tgaaccagct      120
gggcgcgcac gagttctcag ccctgacaga ggtgcttttc cacttcctaa ctgagccaaa      180
agaggtggaa agatttctgg ctcagctctc tgaatttgcc accaccaatc agatcagtct      240
tggctccctc agaagcatcg tgaaaagcct ccttctggtt ccaaatggtg ctttgaagaa      300
gagtctcaca gccaagcagg tccaggcgga tttcataact ctgggtctta gtgaggagaa      360
agccacttac ttttctgaaa agtggaagca gaatgctccc accctctggt gatgggccat      420
aggtcagact ctgatgatta accagctcat agatatggag tggaaatttg gagtgacatc      480
tgggagcagc gaattggaga agtgggaag tatatttta caactaaagt tggtggttaa       540
gaaaggaaat caaaccgaaa atgtgtatat agaattaacc ttgcctcagt tctacagctt      600
cctgcacgag atggagcgag tcagaaccag catggagtgt ttctgctgat ttctgtccct      660
gcatctcccc tggccccgtt ccctgccctc ctcccttccc tgggtgactg ctctgagagg      720
cacttcactc acaggcctgt gggatgctcc atggggccct gctggctcca tggggcccag      780
gtgcaaaggg tttctgaaaa acagcaggat taagtactga agagcccaa cacaattacc       840 ctgtaaactc tctgttaggg caaccaccac cacctgtctt ccaggacaca ttttagata       900 ctctgacagg ccactgcatc tcagattcag gggagaaaat aagttgtcac ctccccttca      960
aagttccaga gtaaacaaat ggtgccatca ttcaagataa catgctgatc accctcctcc     1020
caaaaagcaa gagcttgttt atggctgagg aatcggcgga ttgtctgaat gacacatata     1080
cagagccccc acggatttct gcacactctg gtctgtgct ggtggaacat tgccaatcag      1140
ttcttaatga ggcacctgtg tgtaaataca tgcttggtct tctctgcaga gaactgaggc     1200
taaactctgt ccctacttct ggttttgccc tgtcatgtcg taacgaggtg ggcctttga     1260 ggccatttta gtttgagttc gaaccaacca cctctgttgg ttagatgatg aataaaaagg     1320
ttctgaagaa aaaaaaaaaa aaaaaaaaaa aaaaaa                                 1356
```

<210> SEQ ID NO 3
<211> LENGTH: 100
<212> TYPE: DNA
<213> ORGANISM: Homo sapiens
<220> FEATURE:
<223> OTHER INFORMATION: TSAP11

<400> SEQUENCE: 3

```
tcggtcatag cggttccaag attagcttct actgcttcct gtagcttggc taatatactc       60
tgctttacag ctgatgatat ggtgttgtta aaaaaaaaa                              100
```

<210> SEQ ID NO 4
<211> LENGTH: 467
<212> TYPE: DNA
<213> ORGANISM: Homo sapiens
<220> FEATURE:
<223> OTHER INFORMATION: TSAP12

<400> SEQUENCE: 4

```
tcggtcatag taaattcagc atgaaagaga atattacaga aaagacagca gcagaagcat       60
tagcattatc taatatttat atatgttatc aacataacac agcagtaaaa gtttaaatg      120 catatcaatg ggtaccatgt ctaaaaatta ctatagtacc tatttagtgt attggatatt      180
tttcttaaag agtgtttgct gtaactagaa cagcataata catgatttag tacagttaat      240
tcttattgat taaataatgt atttatgtac tgaagaaagt gaaaggaga cagatatttt      300
```

```
ttgcttcatt ttgattccag atttaacatt taaatgaaga ttccaaagga ccatgacatg      360
tcattattta actgaaatgg gcttcaaaat atttaaaaga cggtatgatt tgtatctaaa      420
cagcaaggtg gcaccagata cacgtaatgc tactggccta tgaccga                    467
```

<210> SEQ ID NO 5
<211> LENGTH: 1547
<212> TYPE: DNA
<213> ORGANISM: Homo sapiens
<220> FEATURE:
<223> OTHER INFORMATION: TSAP13 PROTEASOME HOMOLOGUE

<400> SEQUENCE: 5

```
ttttttttttt tttttttttt tttttttaaca aagcagaggg gtttattata ggaacattct     60
caaactgcaa cggaaaagat gtccgtacag gtggatgggg atggagatcc acctcggagt     120
acacagactt caggggggcct cctgcctggc acgttctttc tctcccgtat cacctaagac    180
cctgagacct ccaccctctg caggagagac ccacaaagaa gcctcctccc tgtggcctgg    240
ctcccatcag ggacagtcct gttttagag caagaacagt ctgtacttca gacaggatcc     300 caaccccac ccaaattcaa tgtcgaccgt ctgagcagcc agcttcattg gctgcaaacg      360
cctctctcag gtgagtcaaa ggagacacga cggggaacca gggggcccta ggtgaggatg    420
tcatgggcct ggtgctccac cagcatctcc atgctcttca catccgtgca ccagaactcc    480
aggcggtcct tcattccctt gatctgttgc aaatccaaca ctcggggctg cacccaggtc    540
atgtggactc gtttgtccac ctcgtctata ctgcctttca ccagccccac cgaaagggcc    600
ttcatcacca gaagctccac ctcattcact gtgattttag cacttttggc aatttcttca    660
aaagtgagtt gtctgtgatt ggcaggtcgt gtgaaagtca tctccatgag gcacaacaac    720
tgaattttcc tcagaagctg ggcttcatta gctgctaaat caggctgctg gccccaggca    780
gtcttcagag tctggaaccg ctctacgttg ccactgttga aggcatagag ggtgtcaatc    840
agccactgcc ggtcagtatt cctcagggac tccagcacag ggtgcatgag gagttctcca    900
aagttaaaaa ctccctcgcc gagaagtcct gctagcccca gcgtgaaggc tctctcctgc    960
tgctcagaca ctggtagatc cttgatgtca acacagccca aaaaccgcag agcatctttg   1020
tagtaggacg cgtggtttcc gattgtttga tagtatttac tggagagatc atagaaacga   1080
ctgtgaaccg atgtcacacc aggaaggttg ttgagcattt cttcaacatc ttcaattgtt   1140
tcctttgtaa cctgtaggtc cccgatgttt aatttagag ctccaattgc tgttttacac    1200
aggatcactg cctcatcact acttttcacc ttctcacgag tcttttccag aaaagtaaga   1260
gccacattag gatcagtcat ctgtctaact acgtgaagaa tgattccac gagggacaga    1320 ggattcaccc tgtgttcaaa ttcactgata aagttttcat aaagcttaat gagaccatct   1380
ccttgggcaa agcacggatc ctgcacaaaa tcaagcacct gaagtgtcag ctgatgccac   1440
aacttcttcg tgtagagctc ctccagacgg tgccacacag cgggctgccc gggcccggag   1500
ctctggctct gctgtaggaa gcccggtacg tccttcatga cagcagg                 1547
```

<210> SEQ ID NO 6
<211> LENGTH: 102
<212> TYPE: DNA
<213> ORGANISM: Homo sapiens
<220> FEATURE:
<223> OTHER INFORMATION: TSAP14

<400> SEQUENCE: 6

```
ggaaccaatc ctaaagaata ttcttacata taataaagaa ttcccatttg atgttcagcc      60
```

```
tgtcccatta agaagaattt tggcacctgg taaaaaaaaa aa                     102

<210> SEQ ID NO 7
<211> LENGTH: 1825
<212> TYPE: DNA
<213> ORGANISM: Homo sapiens
<220> FEATURE:
<223> OTHER INFORMATION: TSAP15

<400> SEQUENCE: 7
tcggcctttc acctcttcac ttatccttag tcccagtagc caggatacct gatggccacg    60
tgtgccttgg ccacgggagg ctgctgagat tggccacgtg gctgggctgg gtggtggcct   120
cactctccca cagagctgga aatgggggt ggggacaga ttcttacgga aattttttta   180
cctgacttgc tatgaaaaaa ctcatcacac aagaagagaa acagtaacct cactttgaaa   240
attagctcca ctcaagacta gtccacgaac gagacccgcc ttttctacac aggatccaag   300
ctcacgagaa gcagccagag tgccccgcct ccgccggctc tggtctgcca ttcgccagtg   360
cagggatctg gcatggacca gatgtggcga atggcagcac agcgcggtgg ctgggtctgc   420
acactggcct ctgcagccag atttctatat tgggagtttt ttaaaaagac atttcatagc   480
caacaagaat cagtagaagt gctgggagca gcagctgggg aagctgccgc ccacgggctc   540
tgccccttcc agctggagcc gccgtgcct ccaggggcca agaggatgat gtcgtggcct   600
ccattctcgt ttctatgcag ccccatagtc caaggacacc cagtccacat ctaccatata   660
gcaagtttag taagggaagg cagcatacgt cccagggaca gtgggtttgg atctgtctag   720
aacagcggtt tgtggctgtg gcccagctcc gagagtgata tttgctctgg taggtgaggg   780
cctgagggta catttctcca cctgtgcccc ctcatgttca cagaggattt cagcagctgc   840
aactgcgcac gccaggtggg gaagggtggg ggtgggcctg gttgccccat gttaggaaat   900
cactaccagt caggtgggc tggggctggg tggacaggat caggattccc ttgaaagccc   960
aggcagggtg agcagtccca gtggtcctag tgccgcatca gatccaggtg ggtgagggca  1020
ggaggccatg cggaggagcc gtggatctgc ccacacatag gctactggaa tagtttaacc  1080
cagcaacttt cctttttata aaacaacaaa tcggttcaac tctgtctgca aattaacagc  1140
tgaacacctg caactgaaat gtttttgat ccgacgtact gaaatacgga agtcatgctc  1200
ttcccaccct ccacccacca gagtggaacc cgctgcaaaa tccccagcct taattcttgc  1260
ttcaggaccc agaccggtgt cttgctctag ggcaacccag ggcagagggg ccaggtctgc  1320
ccagcgttta ccactgctgt caagcacagc ccttggcacc atacgggcca tcctcagtga  1380
ggcagccccc cataggcttc cgcaagctct ggtcccgaag aggctgtgcg agcccttccc  1440
ggccctcccc aggccccccg cccctcctc tgcctgctgc gtggaggcag ccatgggaag  1500
gagcccaggg gagctggcct gggggagcga agcccatgtt cgcttcctga cttagagctg  1560
ggggggggtgg ggggtgggc ttgttcccct gcagtatctg ttctgtgaag tttgttaaat  1620
gtaaggaaag cttaaattct tgtatctttta aaagagaaaa tcttatttaa cccttttgtg  1680
ttctagattt acttacacac atagcctaga gctcagtttt agttttaaca ttgtgaaaat  1740
attaaaagaa tcttgtaact ttattctttt ttctcctgct gaaaaaaaaa attaaaccaa  1800
tcgtatgaaa aaaaaaaaaa aaaaa                                      1825

<210> SEQ ID NO 8
<211> LENGTH: 90
<212> TYPE: DNA
```

```
<213> ORGANISM: Homo sapiens
<220> FEATURE:
<223> OTHER INFORMATION: TSAP16

<400> SEQUENCE: 8
tggattggtc caggattggg gttttgctag tccatagcaa ttcgaagggc agtgggctag    60
tgttatgaga atattggcaa aaaaaaaaa                                      90

<210> SEQ ID NO 9
<211> LENGTH: 131
<212> TYPE: DNA
<213> ORGANISM: Homo sapiens
<220> FEATURE:
<223> OTHER INFORMATION: TSAP17

<400> SEQUENCE: 9
ctgcttgatg taggagggat taagttagta tttcccgtat cgaccaagac aaaattacaa    60
tatacgcata acaaagacaa acaccagtta cttggctcaa tatccaagtt ttaacctagc   120
aaaaaaaaaa a                                                        131

<210> SEQ ID NO 10
<211> LENGTH: 121
<212> TYPE: DNA
<213> ORGANISM: Homo sapiens
<220> FEATURE:
<223> OTHER INFORMATION: TSAP18

<400> SEQUENCE: 10
ggaaccaatc ccaacacaac tggattctac tgaaattacc acatatttga ggtccacaag    60
cacaagtata gatctaatgc aaactgggct cagattagca gatccatgcc aaaaaaaaaa   120
a                                                                   121

<210> SEQ ID NO 11
<211> LENGTH: 893
<212> TYPE: DNA
<213> ORGANISM: Homo sapiens
<220> FEATURE:
<223> OTHER INFORMATION: TSAP19

<400> SEQUENCE: 11
atggagggcc acatctgcca gagcctggag tctgcgaagg ccgggacccg gttcccggc     60 ccacagtggg ggtgtgcaaa cccgagagaa ctgggttgca aattcgtgaa gaatcagcat   120
catgtttggc agctgagtat tggagccagg agcctgccat gaggttttga aacagagtg    180 ctgttttaga gctggcagca gcatctcagc ccaagagaag gttatattcc cagaggatgt   240
cagtcccaag gaccagtagc tgccatcagt ttggattctg aaaactaact ggcatcaaca   300
ctgggtgtag aaacatgctt gccttatgta tcagaggaca tgctcagcag atccaagaga   360
tatatttggc aactttttct agaaaaggca cattgggtat cattcattac attcttgagt   420
tttttttggt ttttttttttt tttttgaga cagtcttgct gtattgccca ggctggagtg   480
tggtggcaca atcacagctc attgcatcct caatcaccca ggcctaagca atcctcccac   540
cttgtagctg ggactacagc tcacagcaca cctggctaaa atttttttttt tgttgagacg   600 gattctctat gttgcccagg ctggtctcag gctcctgggc tcagatggtc ctcctgcctc   660
agcttccaaa ggcacaggcc aagttgtagc tttgtccctt gccatcatgc ccaacaagag   720
gttctatacc ttttaatgaa ttgactttca taaattggtt atgttggtgg gcaagttctt   780
taagctggaa attgtaaatt cctcctgaaa tgttttttca tgcagttacc atgaactaat   840
```

```
actacaataa aggatggtct tgggtgtcaa aaaaaaaaaa aaaaaaaaaa aaa        893

<210> SEQ ID NO 12
<211> LENGTH: 151
<212> TYPE: DNA
<213> ORGANISM: Homo sapiens
<220> FEATURE:
<223> OTHER INFORMATION: TSAP20

<400> SEQUENCE: 12
gatctgactg tagggactat attcattact gctggactat gctgctttcc ccaacccct   60 aggattttaa aaatagcacg ctgcacttga acagggaa gacactgtat aacatccaaa   120
tgttcttctt ccctagaggc caaaaaaaaa a                                 151

<210> SEQ ID NO 13
<211> LENGTH: 1295
<212> TYPE: DNA
<213> ORGANISM: Homo sapiens
<220> FEATURE:
<223> OTHER INFORMATION: TSAP21 SNARE HOMOLOGUE

<400> SEQUENCE: 13
atccagcgcc agctggagat catgggcaag gaagtctcgg gcgaccagat cgaggacatg   60
ttcgagcagg gtaagtggga cgtgttttcc gagaacttgc tggccgacgt gaagggcgcg  120
cgggccgccc tcaacgagat cgagagccgc caccgcgaac tgctgcgcct ggagagccgc  180
atccgcgact acacgagct cttcttgcag atggcggtgc tggtggagaa gcaggccgac  240
accctgaacg tcatcgagct caacgtacaa agacggtcg actacaccgg ccaggccaag  300
gcgcaggtgc ggaaggccgt gcagtacgag gagaagaacc cctgccggac cctctgctgc  360
ttctgctgtc cctgcctcaa gtagcaggcc ggcccgggcc gccaccgccc atcccagacc  420
atggagcgcg ctgggaagga cgtcaccaaa gccgggagct ctgccctgca gggagttgcc  480
ccaacccttt ccggaactca gtctttagaa aagaaacgcc aggttcaaga attgcaaacc  540
agcctgtgct tggaaagatg gttagttgat accgtccgat gattcttcag taaagataga  600
ttcccacaaa gttgtgcaat gtcattatat gacaccttgc actcttaccg tcttgacaga  660
agccaagtaa ggaactgaag ttgtatctga ctgtagggtg aatgtctgag gcctgcctcc  720
taataaagac tcaaggagga agtcaattgg gcatctgcta atagaatgaa ctcatgatgg  780
aaacttcagt tcatttactt tgtccctgaa aattccctgg ttctgttcca ttttgagcga  840
aattggcctt gggaaaaacc acgttcttcc tttccgattc ttcatccggt ctacggctat  900
gcaattcctc cccaaatata gatcttattt ctgctcattt cccctactta ttaaaatcac  960
accaaacact tactattttc ttatctcttt cacttttaa atatctttca ccaggttata 1020
ttttggtatt attttccaa acattttaa gcactgaata tcgaacaagc actcaaattg 1080
aagtatcagt catgttttgt gtattttcg ctgataaaaa ttatttaaca tttatatttt 1140
tacttgatta catatgcaca tgtatgtaaa tgtaaaatac taatattcac taatatatgt 1200
acataatgat caattggttt aacttctttt atgtaagtat ggtatataaa tttcaagacg 1260
aaaaaaaaaa aaaaaaaaaa aaaaaaaaaa aaaaa                           1295

<210> SEQ ID NO 14
<211> LENGTH: 2242
<212> TYPE: DNA
<213> ORGANISM: Homo sapiens
<220> FEATURE:
```

<223> OTHER INFORMATION: TSAP22

<400> SEQUENCE: 14

| | | | | | |
|---|---|---|---|---|---:|
| agggctcgag | cggccgcccg | ggcaggttgt | gttcttaatt | tgcttttccc | ttgtgagtcc | 60 |
| tgcatcattt | gaaaatgtcc | atgcaaagtg | gtatcctgag | gtgcggcacc | actgtcccaa | 120 |
| cactcccatc | atcctagtgg | gaactaaact | tgatcttagg | gatgataaag | acacgatcga | 180 |
| gaaactgaag | gagaagaagc | tgactcccat | cacctatccg | cagggtctag | ccatggctaa | 240 |
| ggagattggt | atggaatcct | gtgttttttcc | tcctccttgt | acctctttta | ttgtagtgac | 300 |
| agactggagt | ccagtctggg | aaaggagggt | gtgtgtctcc | cactcagggc | ctggtgtact | 360 |
| cttggggaac | cagctggcaa | ggccctctgg | gtcttaacgt | cagcgttgga | aggtggaagc | 420 |
| agggctggga | gccggcagaa | ggcgcccggg | ccccaggagc | cgcctcccgc | tggtggtgtg | 480 |
| atcagaagag | agtggggtcg | agtgtacatt | gccgtgtggt | cgtgtttcct | gtaggtgctg | 540 |
| taaaatacct | ggagtgctcg | gcgctcacac | agcgaggcct | caagacagtg | tttgacgaag | 600 |
| cgatccgagc | agtcctctgc | ccgcctcccg | tgaagaagag | gaagagaaaa | tgcctgctgt | 660 |
| tgtaaatgtc | tcagcccctc | gttcttggtc | ctgtcccttg | gaacctttgt | acgctttgct | 720 |
| caaaaaaaaa | caaaaaaaag | aaaaagtcg | caaaaaaaaa | aaacaacggt | ggagccttcg | 780 |
| cactcaatgc | caacttttg | ttacagatta | attttccat | aaaaccattt | tttgaaccaa | 840 |
| tcagtaattt | taaggttttg | tttgttctaa | atgtaagagt | tcagactcac | attctattaa | 900 |
| aatttagccc | taaatgaca | agccttctta | aagccttatt | tttcaaaagc | gcccccccca | 960 |
| ttcttgttca | gattaagagt | tgccaaaata | ccttctgaac | tacactgcat | tgttgtgccg | 1020 |
| agaacaccga | gcactgaact | ttgcaaagac | cttcgtcttt | gagaagacgg | tagcttctgc | 1080 |
| agttaggagg | tgcagacact | tgctctccta | tgtagttctc | agatgcgtaa | agcagaacag | 1140 |
| cctcccgaat | gaagcgttgc | cattgaactc | accagtgagt | tagcagcacg | tgttcccgac | 1200 |
| ataacattgt | actgtaatgg | agtgagcgta | gcagctcagc | tctttggatc | agtctttgtg | 1260 |
| atttcatagc | gagttttctg | accagctttt | gcggagattt | tgaacagaac | tgctatttcc | 1320 |
| tctaatgaag | aattctgttt | agctgtgggt | gtgccgggtg | gggtgtgtgt | gatcaaagga | 1380 |
| caaagacagt | attttgacaa | aatacgaagt | ggagatttac | actacattgt | acaaggaatg | 1440 |
| aaagtgtcac | gggtaaaaac | tctaaaaggt | taatttctgt | caaatgcagt | agatgatgaa | 1500 |
| agaaaggttg | gtattatcag | gaaatgtttt | cttaagcttt | tcctttctct | tacacctgcc | 1560 |
| atgcctcccc | aaattgggca | tttaattcat | ctttaaactg | gttgttctgt | tagtcgctaa | 1620 |
| cttagtaagt | gcttttctta | tagaacccct | tctgactgag | caatatgcct | ccttgtatta | 1680 |
| taaaatcttt | ctgataatgc | attagaaggt | ttttttgtcg | attagtaaaa | gtgctttcca | 1740 |
| tgttacttta | ttcagagcta | ataagtgctt | tccttagttt | tctagtaact | aggtgtaaaa | 1800 |
| atcatgtgtt | gcagctttat | agttttaaa | atatttaga | taattcttaa | actatgaacc | 1860 |
| ttcttaacat | cactgtcttg | ccagattacc | gacactgtca | cttgaccaat | actgaccctc | 1920 |
| tttacctcgc | ccacgcggac | acacgcctcc | tggtagtcgc | tttgcctatt | gatggttcct | 1980 |
| ttgggtctgt | gaggttctgt | aaactggtgc | tagtgctgac | gatgttctgt | acaacttaac | 2040 |
| tcactggcga | gaatacaggg | tgggacccctt | cagccactac | aacagaattt | tttaaattgc | 2100 |
| cagttgcaaa | attgtggagt | gttttttacat | tgatcttttg | ctaatgcaat | tagcattatg | 2160 |
| ttttgcatgt | atgacttaat | aaatccttga | atcataaaaa | aaaaaaaaa | aaaaaaaaa | 2220 |
| aaaaaagcg | gccgctgaaa | cc | | | | 2242 |

```
<210> SEQ ID NO 15
<211> LENGTH: 144
<212> TYPE: DNA
<213> ORGANISM: Homo sapiens
<220> FEATURE:
<223> OTHER INFORMATION: TSIP3

<400> SEQUENCE: 15
ggaaccaatc caaatgccca tcaatgatag actagataaa gaaaatatag tacatatgca        60
ccatgtaata ctatgcagcc gtaaaaaaaa aaaaaaaaaa agacagacaa ggccaaggcc       120
aggcacggtg ggtaaaaaaa aaaa                                              144
```

GENES INVOLVED IN THE MOLECULAR PATHS OF TUMOR SUPPRESSION AND/OR RESISTANCE TO VIRUSES

CROSS-REFERENCE TO RELATED APPLICATIONS

This application is a U.S. national stage application, filed under 35 U.S.C. § 371, and claims foreign priority to French patent application No. 98/10077, filed Aug. 5, 1998.

BACKGROUND OF THE INVENTION

The present invention relates to the revelation of genes involved in the molecular pathways of tumor suppression and/or resistance to viruses.

1. Field of the Invention

The present invention has been made possible by the isolation of cDNA corresponding to messenger RNAs expressed or repressed during tumor suppression and/or during the process of apoptosis induced by the p53 suppressor gene.

2. Description of the Art

One of the most important suppressor genes involved in apoptosis is the p53 gene. When functioning normally, this gene controls cell growth and the process of apoptosis; in particular, it is this gene which blocks cell growth and which must induce the apoptotic process in order to avoid the development of a cancer. It has thus been demonstrated that mice nullizygous for p53 are much more sensitive to the formation of tumors. The fact that, in cancers, the p53 gene is very often modified and leads to the production of proteins incapable of vehicling the message of apoptosis has also been demonstrated.

It is this particularity which has been used in the context of the present invention.

Specifically, the present invention is based on the observation that it is not possible, or at least that it appears to be very difficult, to set up a direct substitution therapy when there is dysfunctioning of the p53 gene. Specifically, p53 which is mutated, as it is in cancer, will annul the physiological effect of normal p53.

It has therefore been necessary to abandon, at least initially, the idea of a substitution therapy acting directly on p53.

The present invention has, therefore, endeavored to study the genes located upstream and downstream of p53 in order to bypass the difficulty mentioned above.

In order to isolate the genes activated or inhibited by normal p53 (wild-type p53), an overall combing of gene expression has been carried out in a malignant line (K562) and a derived cell (KS) in which the malignant phenotype is suppressed, more particularly in a cell expressing p53 which is functionally normal (KS) and in a cell not expressing p53 (K562). Comparison of the genes expressed (messenger RNAs expressed in the two types of cell) has made it possible to reveal genes expressed differentially, i.e. expressed in one of the cells whereas they are not expressed in the other (the genes may be activated or inhibited).

It is easily deduced therefrom that these genes are involved in the cancerization process, in one case by their absence and, in the other case, by their presence.

The method used for this differential study is the method described in 1992 by Liang and Pardee (Differential display of eukaryotic mRNA by means of a polymerase chain reaction).

SUMMARY OF THE INVENTION

The approach to the problem according to the present invention has made it possible to isolate sequences directly linked to a function. Consequently, unlike the random sequencing of ESTs, the sequences are sequences the function of which is known and which are involved in the process of suppression of the malignant phenotype and/or of apoptosis induced by the p53 suppressor gene, and/or in resistance to viruses.

Thus, the present invention relates to novel sequences and the genes comprising them, and to the use of these sequences, both at the diagnostic and at the therapeutic level, just as for producing models intended to test anticancer and antiviral products.

The present invention relates, first of all, to a nucleotide sequence corresponding to a gene comprising:

(a) a sequence according to one of the SEQ IDs 1 to 15 or an equivalent gene which comprises:

(b) a sequence which hybridizes with one of the sequences according to (a), (c) a sequence which has at least 80% homology with (a) or (b), or (d) a sequence which encodes a protein encoded by a gene according to (a), (b) or (c), or an equivalent protein, and to their use in particular in cancer suppression and/or resistance to viruses and in therapeutic monitoring.

It should be recalled that sequences 1 to 15 constitute only a part of the genes implicated, but that the present invention covers both the nucleotide sequence corresponding to the whole gene and fragments of his gene, in particular when they encode an equivalent protein as will be described hereinafter.

The nucleotide sequences can be both DNA sequences and RNA sequences, or sequences in which some of the nucleotides are unnatural, either in order to improve their pharmacological properties or in order to enable their identification.

The sequences mentioned in (b) are essentially the entire or partial complementary sequences (in particular for the cases mentioned above)

Thus, the invention also relates to the nucleotide sequences of the genes which have strong homology with the genes mentioned above, preferably greater than 80% homology on the essential portions of said genes, namely in general at least 50% of the sequence, preferably the homology will be greater than 90% on these portions.

Finally, when said genes encode a protein, the present invention also relates to the sequences encoding the same protein, taking into account the degeneracy of the genetic code, but also the equivalent proteins, i.e. the proteins producing the same effects, in particular the deleted proteins and/or the proteins which have undergone point mutations.

DETAILED DESCRIPTION OF THE INVENTION

The sequences according to the present invention are more particularly the sequences which are induced or inhibited during cellular apoptosis, in particular those induced by p53 and/or p21 and/or TSAP 3 (HUMSIAH) and/or antisense-TSIP 2 (antisense-PS1). In other words, these sequences correspond to genes the cellular expression of which is activated by one at least of the transfectants chosen from the group comprising the p21 transfectants, the TSAP 3 transfectants and the antisense TSIP 2 transfectants.

Said genes are grouped together as TSAP or "Tumor Suppressor Activated Pathway" and termed from TSAP 9 to TSAP 22, corresponding to SEQ IDs 1 to 14, and as TSIP or "Tumor Suppressor Inhibited Pathay", and termed TSIP 3, corresponding to SEQ ID 15.

The characteristics of the sequences are given in the tables appended herein.

The nucleotide sequences corresponding to the TSAP genes are sequences which are expressed during the process of apoptosis, whereas when they are not expressed, the process of oncogenesis continues. It is therefore advantageous:

to detect any abnormality in the corresponding gene, which abnormality may lead to greater susceptibility to oncogenesis, and to be able to provide a replacement therapy.

It should, moreover, be recalled that these genes may be involved in processes other than the processes of tumor suppression; specifically, p53 is in some ways the guardian of the integrity of the genome and under these conditions the TSAP or TSIP genes are doubtless also involved in this control function. It is, therefore, all of the possible modifications of the genome which may be liable to the detection and to the therapy above. On the other hand, the TSIP genes are expressed during oncogenesis and this expression is decreased, or even inhibited, during apoptosis and tumor suppression; it is therefore, in this case as well, advantageous to detect the possible abnormality of the TSIPs and also to provide an inhibition/blocking therapy.

The replacement therapy may be carried out by gene therapy, i.e. by introducing the TSAP gene with the elements which enable its expression in vivo. The principles of gene therapy are known. Specific viral or nonviral vectors can be used, for example adenoviruses, retroviruses, herpesviruses or poxviruses. Most commonly, these vectors are used in defective forms which will serve as vehicles for TSAP expression with or without integration. The vectors can also be synthetic, i.e. mimic viral sequences, or consist of naked DNA or RNA according to the technique developed in particular by the company VICAL.

In most cases, it will be necessary to provide targeting elements which ensure tissue- or organ-specific expression; specifically, the activation of an uncontrolled phenomenon of apoptosis cannot be envisaged.

The present invention relates, therefore, to all of the vectors described above.

The present invention also relates to the cells transformed with an expression vector as described above, and to the protein which can be obtained by culturing transformed cells.

The expression systems for producing proteins can be both eukaryotic systems, such as the vectors above, and prokaryotic systems in bacterial cells.

I. [sic] one of the advantages of the present invention is that it has demonstrated the involvement of several genes in apoptosis; thus, the overexpression of one of the genes by gene therapy can, for some of them, drive to apoptosis only the cells in which other disturbed genes are already expressed, i.e. malignant cells.

The present invention also relates, as a medicine, to a compound which ensures the cellular expression of at least one of the nucleotide sequences above when it is induced during apoptosis and/or tumor suppression, in particular TSAP 9 to TSAP 22 genes, or conversely, which ensures the inhibition of the cellular expression of at least one cellular sequence as described above when it is inhibited during apoptosis and/or tumor suppression, in particular TSIP 3. It may, for example, be an activated nucleotide which ensures the blocking of the nucleotide sequence or be a monoclonal antibody directed against the protein(s) encoded by the nucleotide sequence.

Moreover, it is possible to envisage approaches other than gene therapy, in particular the use of nucleotide sequences in a sense or antisense strategy, i.e. which can block the expression of TSIP or, on the other hand, which act upstream, promoting the expression of TSAP.

It is also possible to envisage a direct replacement strategy by providing proteins corresponding to TSAP, or inhibitory antibodies corresponding to TSIP.

Finally, it is possible to envisage the use of nonprotein molecules, the activity of which will be to activate TSAP or to mimic the action of its expression product, or to inhibit TSIP or to block the action of its expression product.

These products can be easily tested on the modified cells which are described in the examples, by introducing the products to be tested into the cell culture and detecting the appearance of the apoptotic phenomenon. In the DNA, RNA or protein strategies, the products are of course developed as a function of the sequences which are described.

The present invention relates, in particular, to the use of the medicines above as an anticancer agent.

However, the product of the TSAP 9 to 22 and TSIP 3 genes is also useful as an antiviral agent, as will become apparent upon reading the example.

The present invention also relates, therefore, to the use of the medicines above as an antiviral agent.

In addition, the present invention relates, as a diagnostic agent for determining the predisposition to cancer, to all or part of the sequences according to the invention to be used as a nucleotide probe or as an amplification primer, but also, as a diagnostic agent for determining the predisposition to cancer, to an anticen corresponding to all or part of the proteins encoded by the sequence according to the invention, or the corresponding antibodies, optionally after culturing.

The diagnostic methods are known; they may be, for example, techniques for microsequencing the variable portions after isolation and optional amplification, or methods for RFLP-detection or for simple amplification in particular. Differential techniques can, in particular, make it possible to demonstrate the difference between the normal and abnormal TSAP (or TSIP).

The invention also relates to the models using the sequences above.

Moreover, it should be emphasized that the inventors have demonstrated, by extension of the sequences in accordance with the invention initially revealed, homologies shown by said extended sequences with sequences corresponding to known proteins.

More particularly, besides the homology of TSAP 9 with a mouse chaperonin containing the TCP-1 gene (9), the inventors have brought to light a strong homology shown by TSAP 13 with the p40.5 subunit of the human proteasome (10, 11) and a strong homology shown by TSAP 21 with syntaxin 11 belonging to the group of SNARE proteins (12).

The chaperonins are involved in the process of protein folding and assembly in the eukaryotic cytosol. They are suspected of slowing down this folding by trapping intermediates which otherwise would aggregate. Among the proteins on which the chaperonin containing the TCP-1 gene homologous to TSAP 9 would act, mention may be made of actin, tubulin and the capsid protein of the hepatitis B virus.

The proteasome, in the same way as ubiquitin, is the main component of the major proteolytic system responsible for the degradation of many intracellular proteins, including aberrant proteins resulting from mutations or from environmental stress. The p40.5 subunit of the human 26S proteasome has recently been revealed, as well as its homolog in yeast Nas7p. In humans, the mRNA corresponding to the abovementioned subunit is more particularly expressed in the pancreas, placenta, testicles, heart and skeletal muscle. It appears, moreover, that yeast cells deficient for Nas7p are particularly sensitive to heat stress. This contributes to the suggestion that the function of the 26S proteasome is degraded during a heat stress.

The SNARE (Soluble N-ethylmaleimide-sensitive factor-attachment protein receptor) proteins are proteins the differential expression and the associations of which are involved in the organization of the membrane compartments of cells. These proteins are specifically located in the region of the Golgi apparatus, of the endosomes and of the lysosomes, which suggests that they play a role in the regulation of membrane exchanges using these organelles. More particularly, syntaxin 11 is thought to be located in the post-Golgi region.

It would be advantageous to be able to determine whether the molecular pathways in which the sequences in accordance with the invention are involved have common points with the molecular pathways in which the abovementioned proteins are involved, which would make it possible to envisage novel modes of action on the abovementioned sequences for, for example, therapeutic or diagnostic purposes.

Other characteristics of the invention will become apparent upon reading the example below.

MATERIALS AND METHODS

Cell Cultures

K562, KS, K52 and K53 cells were used as models. The K562 line is a tumor line derived from a chronic leukemia of erythromyeloid type. It is characterized in particular by a Philadelphia chromosome which contains the translocation (9,22) in which there is a rearrangement of the bcr gene with the abl proto-oncogene. This line has, moreover, an abnormal karyotype and overexpresses the myc and pim-1 oncogenes. These lines are described in the reference A. Telerman et al.: A model for tumor suppression using H-1 parvovirus, Proc. Natl. Acad. Sci. USA. Vol. 90, pp. 8702–8706, September 1993.

In summary, a monoclone of K562 was infected with the H-1 parvovirus. This infection caused a massive death of the cell culture. After maintaining this culture for a period of two months, the KS clone was isolated. The same experiment carried out a second time provided, after three months of incubation, the KS2 and KS3 clones.

Using the same approach, the inventors derived, from a population of U937 malignant cells, the US3 and US4 lines, which are resistant to the H-1 parvovirus and which show suppression of the malignant phenotype. These lines are described in reference (7).

M1 myeloid leukemia-cells and M1 cells were stably transfected with a heat-sensitive mutant val 135 p53 (LTR6).

These cells are cultured on RPMI 1640 medium with 10% FCS, at 5% of $CO_2$ at 37° C. (3). For the temperature modification, the cultures are placed in a second incubator at 32° C.

U937 line transfected with $p21^{WAF1}$: the complete coding portion of the cDNA of the $p21^{WAF1}$ gene was cloned into the vector pBK-RSV (Stratagene, La Jolla, Calif.). 3.5 million U937 cells were transfected with 20 micrograms of DNA/30 micrograms of Lipofectin (Life Technologies).

The stable transfectants were selected using 1.5 mg/ml of G418 (Sigma). The characteristics of this Line portray in particular a suppression of the malignant phenotype.

U937 line transfected with TSIP 2 (PS1) in the antisense position: the complete coding portion of the cDNA of the TSIP 2 (PS1) gene was cloned, in the antisense position, into the vector pBK-RSV (Stratagene, La Jolla, Calif.). 3 million U937 cells were transfected with 20 micrograms of DNA/30 micrograms of Lipofectin (Life Technologies).

The stable transfectants were selected using 1.5 mg/ml of G418 (Sigma). The characteristics of this line, portraying in particular a slowing down of growth, activation of apoptosis and suppression of the malignant phenotype, have been described in reference (8).

U937 line transfected with TSAP3 (HUMSIAH): the complete coding portion of the cDNA of the TSAP 3 gene was cloned into the vector pBK-RSV (Stratagene, La Jolla, Calif.). 3 million U937 cells were transfected with 20 micrograms of DNA/30 micrograms of Lipofectin (Life Technologies).

The stable transfectants were selected using 1.5 mg/ml of G418 (Sigma). The characteristics of this mine comprise in particular activation of apoptosis and suppression of the malignant phenotype.

Study of the Differential cDNAs

In order to carry out the tests under standard experimental conditions and to obtain total reproducibility of the results, the following modifications to the protocol of origin (1) were carried out:

PolyA+ mRNAs purified twice on an oligodT column using Fast Track (Invitrogen, San Diego Calif.) are always used. After reverse transcription (M-MLV Reverse Transcriptase, Gibco BRL) on 0.05 µg of polyA+ using 20 µM of each of the dNTPs (Boehringer-Mannheim), no added dNTP is added to the final PCR mixture. A "hot start" at 94° C. for 5 minutes is carried out before the PCR (GeneAmp PCR system 9600 Perkin Elmer Cetus). The samples are cooled rapidly on iced water. A "touch down" (2) of 10 cycles of 50° C. to 40° C. is carried out (94° C. 30 seconds—50° C. 1 minute—72° C. 30 seconds), followed by 35 cycles (94° C. 30 seconds—40° C. 1 minute—72° C. 30 seconds, and a final extension of 5 minutes at 72° C. The PCR products are separated on nondenaturing 6% polyacrylamide gels (4). The gels are exposed without drying. Each differential presentation is carried out by comparing M1S6 and LTR6 at 37° C. and after incubating the two cell lines at 32° C for 4 hours.

The differential presentation procedure is repeated in 3 different experiments in order to confirm total reproducibility.

The differentially expressed bands are cut out of the gel, eluted and reamplified (1). The PCR products are subcloned using the TA-cloning system (Invitrogen, San Diego, Calif.), following the instructions provided.

For each ligation reaction, 10 recombinant clones are sequenced using the ABI automatic system.

RNA Extraction, Analyses and Northern Blot Probes

The total RNA is extracted with Trizol (Life Technologies). The poly1+ [sic] RNAs are prepared using the OligotexdT kit (Qjagen, Calif.). 30 µg of the total RNA or 2 µg of polyA+ RNA are separated on 1% agarose, 1×MOPS/2% formaldehyde gel and transferred onto nylon membrane (Hybond N+, Appligène, France) as has been described previously (5). The Northern blots are hybridized with probes labeled with $P^{32}$ on the TSAP and TSIP inserts, and washed as described previously (5). In order to verify the induction of the wild-type p53 function, the Northern blots are hybridized with a cyclin G probe (6). By way of control for the amount of mRNA loaded, the blots are hybridized with a GAPDH probe. Various Northern blots (Clontech Calif.) are used under identical conditions and hybridized for control with a β-actin probe. The Northern blots are exposed for 10 days at −80° C.

EXAMPLE 1

The desired aim is to characterize the molecular pathways which lead to the suppression of cancer.

The following hypothesis was made to develop a model: if it was possible to select, from a tumor which is sensitive to the cytopathic effect of the H-1 parvovirus, the cells which were resistant, this resistance might be due to a change in their malignant phenotype. It was possible to demonstrate this for the KS cells selected from the K562 erythroleukemia cells. Unlike the parental K562 line, the KS, KS2 and KS3 clones are resistant to the cytopathic effect of the H-1 parvovirus. In addition, the tumorigenicity of the KS, KS2 and KS3 cells is reduced by 90%, while, when cultured in soft agar, the tumorigenicity of these same KS lines in vivo when injected into Scid-Scid immunosuppressed mice is reduced. At the molecular level, it could be noted that this suppression of the malignant phenotype went hand in hand with a reexpression of the p53 suppressor gene.

15 cDNAs expressed differentially between the K562 and KS cells were isolated. TSAP 9 is homologous to the chaperoning.

Table 1 shows the molecules characterized, giving the primers and the sizes of the mRNAs detected by Northern blot.

Of these 15 molecules, all are induced in the KS cells, except TSIP 3, the expression of which is inhibited during the suppression of the malignant phenotype.

In transfection experiments, it was also possible to demonstrate that the resistance to the cytopathic effect of the H-1 parvovirus went hand in hand with an intact function of the p53 gene and that cells transfected with p53 mutants became sensitive to the cytopathic effect of the H-1 parvovirus.

The 15 molecules which we have isolated encode, therefore, genes whose overexpression (TSAP 9–TSAP 22) or inhibition (TSIP 3) is associated not only with the suppression of cancer, but also with resistance to the H-1 parvovirus. Consequently, these genes encode molecules which are part of the molecular pathways of cancer suppression and are potential suppressor genes.

In order to more clearly define the p53/p21 activation pathways, the inventors have studied:

the activation of these TSAPs/inhibition of the TSIPs in the heat-sensitive p53 model developed in Moshe Oren, the activation of these TSAPs/inhibition of the TSIPs in the model in which U937 cells are transfected with the p21 gene, the activation of the novel TSAPs/inhibition of the TSIPs in the model in which U937 cells are transfected with the TSAP3 gene, and the activation of these novel TSAPs/TSIPs in the model in which U937 cells are transfected with the TSIP 2 (PS1) gene in the antisense position.

Table 1 below reports results of differential expressions analyzed by Northern blot of the various probes (TSAP 9–TSAP 22, TSIP 3) of the K562/KS model and other U937/US3-US4 models, i.e. in a model of tumor suppression in which the p21gene is activated via the p53 independent pathway. These cDNAs are therefore activated in two different cellular systems of tumor suppression (the K562/K2 erythroleukemia model and the U937/US myelomonocytic model).

According to this table, it is noted that, in the majority of cases, the genes expressed differentially in the K562/KS model are also expressed differentially in the U937/US3-US4 model. Molecular machinery for tumor suppression therefore exists which is common to various types of cancer. This conclusion is also valid for the M1/LTR-6 model. It should be noted, in the latter case, that the absence of signals in certain TSAPs-TSIPs is probably due to the fact that the experiments were carried out in two heterologous systems (human probes on mouse RNA).

TABLE 1

| CLONE WITH DIFFERENTIAL EXPRESSION | 3' AND 5'* PRIMERS | K562/KS cDNA PROBE | HOMOLOGY | K562/KS MODEL mRNA kb | U937/US3-US4 MODEL RESULT | U937/US3-US4 MODEL mRNA kb | M1/LTR-6 MODEL RESULT | M1/LTR-6 MODEL MRNA kb |
|---|---|---|---|---|---|---|---|---|
| TSAP 9 | T11AA-9 | K26 D3 | Chaperonin ◊ | 2.6 | DIFF. EXP. | 2.0 | DIFF. EXP. | 2.6 |
| TSAP 10 | T11AA-9 | K25.0 A11 |  | 1.6 | DIFF. EXP. | 1.6 | NO SIGNAL | 1.6 |
| TSAP 11 | T11AA-9 | K25.0 B7 | EST | 2.9 | NO DIFF. EXP. | 2.8 | NO SIGNAL | 2.9 |
| TSAP 12 | T11AA-9 | K27.1 C7 | EST | 5.5 | NO SIGNAL | 5.5 | NO SIGNAL | 5.5 |
| TSAP 13 | T11AA-23 | K25.1 F3 | Proteasome° | 1.8 | DIFF. EXP. | 1.5 | DIFF. EXP. | 1.8 |
| TSAP 14 | T11AC-5 | K33.2 F10 | EST | 2.5 | DIFF. EXP. | 2.8 | DIFF. EXP. | 2.5 |
| TSAP 15 | T11AG-19 | K22 E3 | EST | 1.6 | DIFF. EXP. | 1.8 | NO SIGNAL | 1.6 |
| TSAP 16 | T11GC-2 | K12.1 F5 |  | 2.8 | DIFF. EXP. | 2.0 | DIFF. EXP. | 2.8 |
| TSAP 17 | T11GC-12 | K16.1 C7 |  | 1.8 | DIFF. EXP. | 1.9 | DIFF. EXP. | 1.8 |
| TSAP 18 | T11GG-5 | K3.1 D2 | EST | 2.0 | NO DIFF. EXP. | 1.8 | DIFF. EXP. | 2.0 |
| TSAP 19 | T11GG-23 | K5.2 E10 | EST | 1.5 | DIFF. EXP. | 1.6 | NO SIGNAL | 1.5 |
| TSAP 20 | T11GG-23 | K5.1 A12 |  | 1.7 | DIFF. EXP. | 1.9 | NO SIGNAL | 1.7 |
| TSAP 21 | T11GG-23 | K5.1 A1 | SNARE△ | 2.1 | DIFF. EXP. | 1.9 | DIFF. EXP. | 2.1 |
| TSAP 22 | T11GG-5 | K3.1 A12 | EST | 2.8 | DIFF. EXP. | 2.6 | DIFF. EXP. | 2.8 |
| TSIP 3 | T11AC-5 | K33.1 B11 | EST | 9.5 | DIFF. EXP. | 9.5 | NO SIGNAL | 9.5 |

*the numbers and sequences of the primers in the 5' position correspond to those reported by Bauer et al.
◊ HUMKG1DD human mRNA for the ORF (human equivalent of mouse chaperonin containing the TCP-1 gene (t-complex polypeptide)).
° p-40.5 subunit of the proteasome (Nas7p)
△ SNARE syntaxin 11
DIFF. EXP. = Differential expression
NO DIFF. EXPR. [sic] = No differential expression Table 2 below summarizes the differential expression of certain TSAP and TSIP clones in various transfectant lines.

It emerges from this table that, in the majority of cases, the p21 transfectants, TSAP 3 transfectants or antisense-TSIP2 transfectants are capable of activating the molecular machinery of tumor suppression common to the U937/US and K562/KS systems.

TABLE 2

| CLONE | P21 TRANSFECTANTS DIFFERENTIAL EXPRESSION | TSAP3 TRANSFECTANTS DIFFERENTIAL EXPRESSION | ANTISENSE TSIP2 TRANSFECTANTS DIFFERENTIAL EXPRESSION |
|---|---|---|---|
| TSAP9 | YES | YES | YES |
| TSAP10 | YES | YES | YES |
| TSAP11 | NO | NO | NO |
| TSAP12 | NO | NO | NO |
| TSAP13 | YES | YES | YES |
| TSAP14 | YES | YES | YES |
| TSAP15 | YES | YES | YES |
| TSAP16 | NO | YES | NO |
| TSAP17 | YES | NO | NO |
| TSAP18 | NO | YES | YES |
| TSAP19 | NO | NO | NO |
| TSAP20 | YES | NO | YES |
| TSAP21 | YES | YES | YES |
| TSAP22 | YES | YES | YES |
| TSIP3 | YES | YES | YES |

Table 3 below recapitulates the characteristics of differential expression of the cDNA clones by Northern blot.

TABLE 3

| cDNA clones | MRNA kb | HOMOLOGY | K562/K [sic] | U937/US | U937 p21 | U937 AS PS1 | U937 SIAH/ TSAP3 |
|---|---|---|---|---|---|---|---|
| TSAP9 | 2.6 | Chaperonin ◊ | D | D | D | D | D |
| TSAP10 | 1.6 | EST | D | D | D | D | D |
| TSAP11 | 2.8 | EST | D | N | N | N | N |
| TSAP12 | 5.5 | EST | D | N | N | N | N |
| TSAP13 | 1.8 | Proteasome° | D | D | D | D | D |
| TSAP14 | 2.5 | EST | D | D | D | D | D |
| TSAP15 | 1.6 | EST | D | D | D | D | D |
| TSAP16 | 2.5 | NO | D | D | N | N | D |
| TSAP17 | 1.8 | NO | D | D | D | N | N |
| TSAP18 | 2.0 | EST | D | N | N | D | D |
| TSAP19 | 1.5 | EST | D | D | N | N | N |

TABLE 3-continued

| cDNA clones | MRNA kb | HOMOLOGY | K562/K [sic] | U937/US | U937 p21 | U937 AS PS1 | U937 SIAH/TSAP3 |
|---|---|---|---|---|---|---|---|
| TSAP20 | 1.7 | NO | D | D | D | D | N |
| TSAP21 | 2.1 | SNARE△ | D | D | D | D | D |
| TSAP22 | 2.6 | EST | D | D | D | D | D |
| TSIP3 | 9.5 | EST | D | D | D | D | D |

D: Differential expression
N: No differential expression
◇ Chaperonin containing the TCP 1 gene
° p40.5 subunit of the proteasome (Nas 7p)
△ SNARE syntaxin 11

References (1) Liang P. & Pardee A. B. (1992) Science, 257, 967–971
(2) Don R. H., Cox P. T., Wainwright B. J., Baker K. & Mattick J. S. (1991) Nucl. Acids Res., 19, 4008
(3) Yonish-Rouach E., Resnitzky D., Lotem J., Sachs L., Kimchi A. & Oren M. (1991) Nature 352, 345–347
(4) Bauer D., Muller H., Reich J., Riedel H., Ahrenkiel V., Warthoe P. & Strauss M. (1993) Nucl. Acids Res. 21, 4272–4280
(5) Sambrook J., Fritsch E. F. & Maniatis T. (1989) Molecular Cloning: a laboratory manual
(6) Okamoto K. & Beach D. (1994) EMBO J., 13, 4816–4822
(7) Nemani M., Linares-Cruz G., Bruzzoni-Giovanelli H., Roperch J.-P., Tuynder M., Bougueleret L., Cherif D., Medhioub M., Pasturaud P., Alvaro V., Der Sarkissan H., Cazes L., Le Paslier D., Le Gall I., Israeli D., Dausset J., Sigaux F., Chumakov I., Oren M., Calvo F., Amson R. B., Cohen D. and Telerman A., Activation of the human homologue of the Drosophila sina gene in apoptosis and tumor suppression, Proc. Nati., Acad. Sci. USA (1996) 93, 9039–9057
(8) Roperch J.-P., Alvaro V., Prieur S., Tuynder M., Nemani M., Lethrosne F., Piouffre L., Gendron M-G. , Israeli D., Dausset J., Oren M., Anson R., and Teleman A., Inhibition of presenilin 1 expression is promoted by p53 and p21 WAF-1 and results in apoptosis and tumor suppression, Nature Medicine (1998) 4, 835–838.
(9) Kubota et al., 1995, Eur. J. Biochem. 230, 3–16,
(10) Hori et al., 1998, Gene, 216, 113–122,
(11) Baumeister et al., 1998, Cell, Vol. 92, 367–380,
(12) Advani et al., 1998, The Journal of Biological Chemistry, Vol. 273, No. 17, 10317–10324.

What is claimed is:

1. An isolated DNA molecule encoding TSAP 21, said isolated DNA molecule consisting of the nucleotide sequence of SEQ ID) NO:13, wherein the expression of said TSAP 21 is activated by p53- or p21-induced apoptosis or tumor suppression.

2. A vector comprising said isolated DNA molecule of claim 1.

3. The vector of claim 2, wherein said vector is a viral vector.

4. The vector of claim 3, wherein said viral vector is adenoviral, retroviral, herpesviral or poxviral.

5. The vector of claim 2, wherein said vector is a plasmid.

6. An isolated or cultured host cell stably transformed with the vector of claim 2.

* * * * *